United States Patent
Mori et al.

(10) Patent No.: US 6,940,083 B2
(45) Date of Patent: Sep. 6, 2005

(54) ISOTOPIC GAS ANALYZER AND METHOD OF JUDGING ABSORPTION CAPACITY OF CARBON DIOXIDE ABSORBENT

(75) Inventors: Masaaki Mori, Hirakata (JP); Yasuhiro Kubo, Shiga (JP); Masahiko Miyoshi, Hirakata (JP); Tamotsu Hamao, Kyoto (JP); Hiroaki Mizui, Neyagawa (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 301 days.

(21) Appl. No.: 10/381,314

(22) PCT Filed: Sep. 19, 2001

(86) PCT No.: PCT/JP01/08128

§ 371 (c)(1),
(2), (4) Date: Mar. 25, 2003

(87) PCT Pub. No.: WO02/25250

PCT Pub. Date: Mar. 28, 2002

(65) Prior Publication Data

US 2003/0178589 A1 Sep. 25, 2003

(30) Foreign Application Priority Data

Sep. 25, 2000 (JP) ........................................ 2000-290986
Sep. 25, 2000 (JP) ........................................ 2000-290987

(51) Int. Cl.⁷ .............................................. G01N 15/06
(52) U.S. Cl. .................................. 250/573; 250/339.13
(58) Field of Search .............................. 250/573, 576, 250/339.13, 345, 343; 356/451

(56) References Cited

U.S. PATENT DOCUMENTS

| 4,499,377 A | | 2/1985 | Presser |
| 4,937,448 A | * | 6/1990 | Mantz et al. ............... 250/343 |
| 5,964,712 A | | 10/1999 | Kubo et al. |
| 6,002,133 A | | 12/1999 | Nelson et al. |
| 6,274,870 B1 | | 8/2001 | Kubo et al. |
| 6,444,985 B1 | | 9/2002 | Mori et al. |
| 6,455,852 B2 | | 9/2002 | Mori et al. |

FOREIGN PATENT DOCUMENTS

| DE | 19649343 | 6/1998 |
| DE | 19731889 | 1/1999 |
| DE | 19750133 | 7/1999 |
| JP | 61-42219 | 9/1986 |
| JP | 61-42220 | 9/1986 |
| JP | 3014652 | 12/1999 |
| JP | 3176302 | 4/2001 |
| WO | WO 98/30888 | 7/1998 |

* cited by examiner

*Primary Examiner*—Que T. Le
(74) *Attorney, Agent, or Firm*—Finnegan, Henderson, Farabow, Garrett & Dunner, L.L.P.

(57) ABSTRACT

In an isotopic gas analyzer, a gas injector (21) is provided for pressurizing a gas specimen in cells (11$a$, 11$b$). The pressurization of the gas specimen virtually produces the same effect as increasing the concentration of carbon dioxide in the gas specimen, thereby improving an S/N ratio for the analysis and hence data reproducibility.

5 Claims, 18 Drawing Sheets

ISOTOPIC GAS ANALYZER AND METHOD OF JUDGING ABSORPTION CAPACITY OF CARBON DIOXIDE ABSORBENT

TECHNICAL FIELD

Isotopic analyses are useful for diagnosis of diseases in medical applications, in which the metabolic functions of a living body can be determined by administering an isotope-containing drug to the living body and then detecting a change in the concentration ratio of the isotope.

The present invention relates to a stable isotope measurement method for spectrometrically analyzing an isotopic gas for determining the isotopic gas concentration ratio on the basis of a difference in light absorption characteristic between isotopes.

BACKGROUND ART

Bacteria called Helicobacter Pylori (HP) are generally known which cause gastric ulcers and gastritis.

If HP is present in the stomach of a patient, an antibiotic should be administered to the patient for bacteria removal treatment. Therefore, it is indispensable to check if the patient has HP. HP has a high urease activity for decomposing urea into carbon dioxide and ammonia.

Carbon has isotopes having mass numbers of 12, 13 and 14, among which the isotope $^{13}C$ having a mass number of 13 is easy to handle because of its non-radioactivity and stability.

If the concentration of $^{13}CO_2$ as a final metabolic product in breath of the patient, more specifically, a $^{13}CO_2/^{12}CO_2$ concentration ratio, can successfully be determined after $^{13}C$-labeled urea is administered to the patient, the presence of HP can be confirmed.

However, the $^{13}CO_2/^{12}CO_2$ concentration ratio in naturally occurring carbon dioxide is 1:100, making it difficult to accurately determine the concentration ratio in the breath of the patient.

There have conventionally been known methods for determining a $^{13}CO_2/^{12}CO_2$ concentration ratio by way of infrared spectrophotometry (see Japanes Examined Patent Publication No. 61-42219 (1986) and No. 61-42220 (1986)).

The method disclosed in Japanese Examined Patent Publication No. 61-42220 employs two cells respectively having a long path and a short path. The path lengths of the cells are adjusted so that a $^{13}CO_2$ absorbance in one of the cells is equalized with a $^{12}CO_2$ absorbance in the other cell. Light beams respectively having wavelengths suitable for determination of the $^{13}CO_2$ absorbance and the $^{12}CO_2$ absorbance are applied to the respective cells, and the intensities of transmitted light beams are measured. According to this method, an absorbance ratio for the concentration ratio in naturally occurring carbon dioxide can be set at 1. Therefore, the absorbance ratio is changed correspondingly to a change in the concentration ratio. This allows for detection of the change in the concentration ratio.

(A) Even if the methods employing the infrared spectrophotometry are used, it is difficult to detect a slight change in the concentration ratio. The sensitivity can be enhanced by using longer cells, but the use of the longer cells increases the size of the isotopic gas analyzer.

Another approach is to provide mirrors at opposite ends of the cells for reflecting the light beams many times. However, the cells each have a greater volume, so that the isotopic gas analyzer has a correspondingly greater size.

It is therefore an object of the present invention to provide a stable isotope measurement method, which can determine the concentrations of component gases with a satisfactory measurement reproducibility and with a higher measurement accuracy by introducing a gas specimen containing carbon dioxide $^{13}CO_2$ and carbon dioxide $^{12}CO_2$ as the component gases into cells, measuring the intensities of light beams transmitted through the cells at wavelengths suitable for analysis of the respective component gases, and processing data indicative of the light intensities, and yet is free from a size increase.

(B) In the methods employing the infrared spectrophotometry, a reference gas having a $CO_2$ concentration of zero, i.e., air having passed through a carbon dioxide absorbent, is filled in the cells, and a reference absorbance measuring process is preliminarily performed for accurate measurement of the absorbances of $^{12}CO_2$ and $^{13}CO_2$.

Where the carbon dioxide absorbent is used as described above, the carbon dioxide absorbent is gradually deteriorated, and it is difficult to determine when the absorbent needs replacement.

The replacement time may be indicated on the basis of the number of times of the analysis, or determined on the basis of a change in the color of the carbon dioxide absorbent which is adapted to be colored by a reaction with carbon dioxide.

Where the determination of the replacement time is based on the number of the times of the analysis, however, the analysis may suffer from an error which occurs due to variations in the absorption capacity of the carbon dioxide absorbent depending on production lots.

Where the carbon dioxide absorbent variable in color is used, the color of the absorbent returns to its original color when the air flow is stopped. Therefore, it is difficult to determine the replacement time.

It is therefore another object of the present invention to provide a method of judging the absorption capacity of a carbon dioxide absorbent, which can accurately indicate a replacement time of the carbon dioxide absorbent by quantizing the degree of the deterioration of the carbon dioxide absorbent.

SUMMARY OF THE INVENTION (A) The stable isotope measurement method according to the present invention pressurizes a gas specimen in the cell, measures an absorbance of the component gases, and determines a concentration ratio of the component gases on the basis of a calibration curve.

The pressurization of the gas specimen virtually produces the same effect as increasing the carbon dioxide concentration in the gas specimen, thereby improving an S/N ratio and hence the measurement accuracy and the measurement reproducibility without the need for increasing the lengths of the cells. Further, the size increase of the analyzer can be obviated.

Where the internal pressures of the cells are increased to 2 atm by the pressurization, a sufficient effect can be provided (see an embodiment to be described later).

(B) The method of judging the absorption capacity of the carbon gas absorbent according to the present invention comprises the steps of: performing a first light intensity measuring process by introducing air having passed through a vessel containing the carbon dioxide absorbent into the cells; performing a second light intensity measuring process by introducing air not having passed through the vessel containing the carbon dioxide absorbent into the cells; and judging the absorption capacity of the carbon dioxide absorbent on the basis of a light intensity measured in the first light intensity measuring step and a light intensity measured in the second light intensity measuring step.

With this arrangement, the air having passed through the vessel containing the carbon dioxide absorbent and the air not having passed through the vessel containing the carbon dioxide absorbent are respectively optically analyzed to determine how much carbon dioxide is absorbed by the carbon dioxide absorbent by comparing the air having passed through the vessel with the air not having passed through the vessel.

In the judgment method, the ratio of the light intensity measured in the first light intensity measuring step to the light intensity measured in the second light intensity measuring step is compared with a threshold for judgment of the absorption capacity of the carbon dioxide absorbent.

In accordance with the present invention, variations in the judgment among individuals can be eliminated. Further, the carbon dioxide absorbent can be used up to its capacity, allowing for highly reliable isotopic gas spectrophotometric analysis. Further, variations in the absorption capacity of the carbon dioxide absorbent depending on production lots do not affect the isotopic gas spectrophotometric analysis.

BRIEF DESCRIPTION OF THE DRAWINGS

FIG. 8 is a diagram illustrating a gas flow path to be employed when air for sample gas dilution is sucked in;

BEST MODE FOR CARRYING OUT THE INVENTION

An embodiment of the present invention will hereinafter be described in detail with reference to the attached drawings. In this embodiment, a $^{13}C$-labeled urea diagnostic drug is administered to a patient, and then a $^{13}CO_2$ concentration in breath sampled from the patient is spectrophotometrically analyzed.

I. Breath Test

First, breath of the patient is sampled in a breath sampling bag before the administration of the urea diagnostic drug. Then, the urea diagnostic drug is orally administered to the patient and, after a lapse of about 20 minutes, breath of the patient is sampled in another breath sampling bag in the same manner as in the previous breath sampling.

The breath sampling bags obtained before and after the drug administration are respectively attached to predetermined nozzles of an isotopic gas spectrophotometric analyzer, and an automatic analysis is. performed in the following manner.

II. Isotopic Gas Spectrophotometric Analyzer

Figure 1:
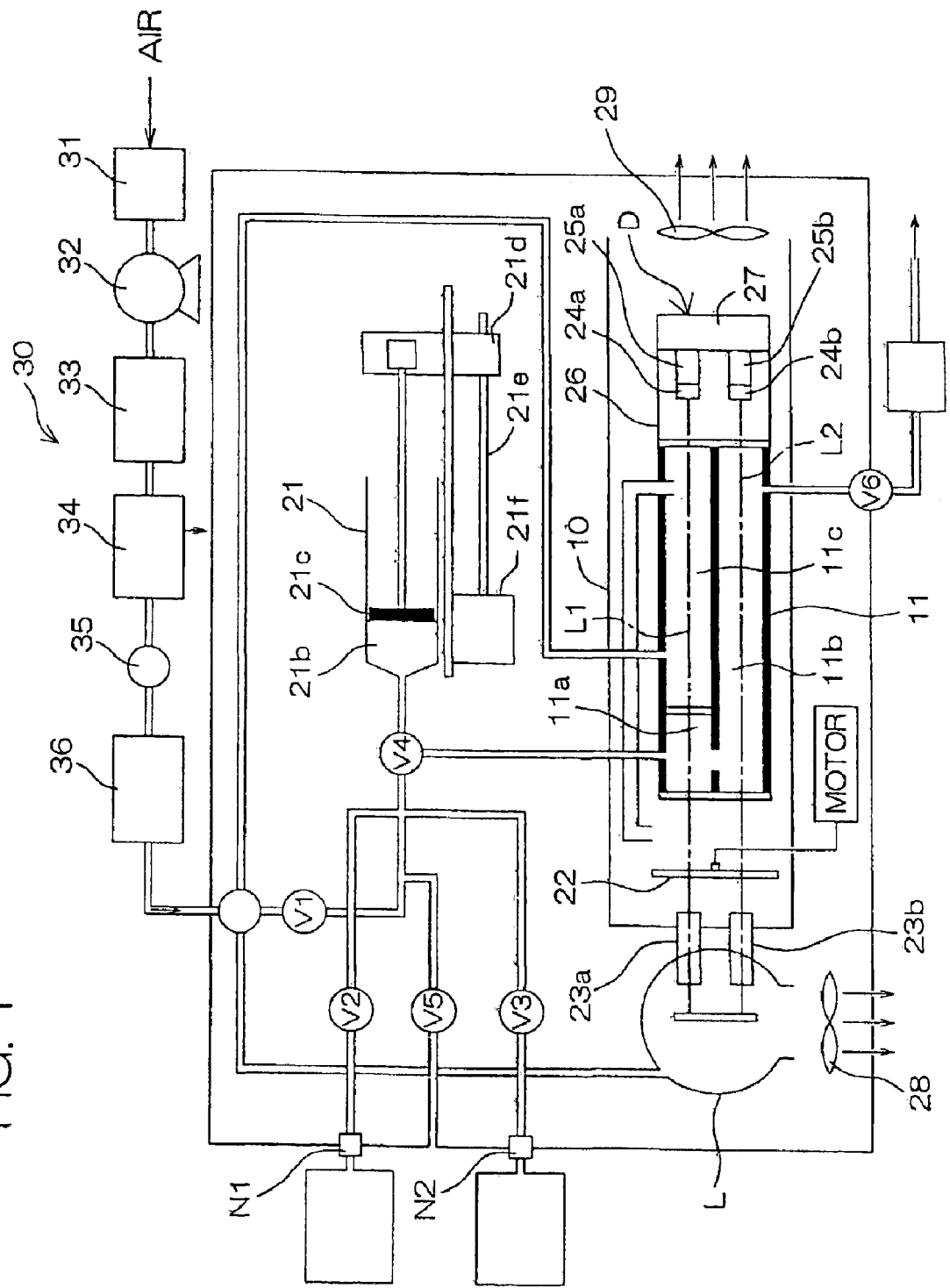
FIG. 1 is a block diagram illustrating the overall construction of an isotopic gas spectrophotometric analyzer.

FIG. 1 is a block diagram illustrating the overall construction of the isotopic gas spectrophotometric analyzer.

The breath sampling bag containing the breath obtained after the drug administration (hereinafter referred to as "sample gas") and the breath sampling bag containing the breath obtained before the drug administration (hereinafter referred to as "base gas") are respectively attached to the nozzles N1 and N2. The nozzle N1 is connected to an electromagnetic valve V2 (hereinafter referred to simply as "valve") through a metal pipe (herein after referred to simply as "pipe"), while the nozzle N2 is connected to a valve V3 through a pipe. Further, a pipe for introducing air is connected to a valve V5.

A reference gas supplied from a reference gas supplying section 30 (which will be described later) flows into three paths. The reference gas flowing into one of the paths is fed into an auxiliary cell 11c, and the reference gas flowing into another of the paths flows into a valve V1. The reference gas flowing into the other path flows into a light source unit for regulation of the temperature of the light source unit.

The reference gas flowing into the auxiliary cell 11c is discharged into a cell chamber 10 from the auxiliary cell 11c.

An outlet of the valve V1 is connected to one port of a three-way valve V4, and another port of the three-way valve V4 is connected to a gas injector 21 for quantitatively injecting the sample gas or the base gas. The gas injector 21 is a syringe-like configuration having a piston and a cylinder. The piston is driven by cooperation of a pulse motor, a feed screw coupled to the pulse motor and a nut fixed to the piston (which will be described later).

The other port of the three-way valve V4 is connected to a first sample cell 11a for measuring a $^{12}CO_2$ absorbance. Pipes extending from the valves V2, V3 and V5 join a pipe which connects the valve V1 and the three-way valve V4.

The cell chamber 11 includes the first sample cell 11a having a small length for measuring the $^{12}CO_2$ absorbance, a second sample cell 11b having a great length for measuring a $^{13}CO_2$ absorbance, and the auxiliary cell 11c through which the reference gas flows. The first sample cell 11a communicates with the second sample cell 11b, so that the gas introduced into the first sample cell 11a directly enters the second sample cell, 11b and discharged through a valve V6. The reference gas is introduced into the auxiliary cell 11c.

The first sample cell 11a has a volume of about 0.6 ml, and the second sample cell 11b has a volume of about 12 ml. Specifically, the length of the first sample cell 11a is 13 mm, and the length of the second sample cell 11b is 250 mm. The auxiliary cell 11c has a length of 236 mm. Sapphire windows pervious to infrared radiation are provided on opposite end faces of the cell chamber 11. The cell chamber 11 is enclosed by a heat insulating material such as polystyrene foam (not shown).

A reference character L denotes the infrared light source unit. The infrared light source unit L includes two waveguides 23a, 23b for projection of infrared light beams. The infrared light beams may be generated in any manner. For example, a ceramic heater (surface temperature: 450° C.) or the like may be used. A rotary chopper 22 is provided for blocking the infrared light beams on a predetermined cycle.

The infrared light beams projected from the infrared light source unit L respectively pass along a first light path L1 extending through the first sample cell 11a and the auxiliary cell 11c and along a second light path L2 extending through the second sample cell 11b. (see FIG. 1).

A reference character D denotes an infrared detector for detecting the infrared light beams having passed through the cells.

The infrared detector D has a first wavelength filter 24a and a first detection element 25a provided in the first light path, and a second wavelength filter 24b and a second detection element 25b provided in the second light path.

The first wavelength filter 24a is designed to transmit infrared radiation having a wavelength of about 4280 nm for the measurement of the $^{12}CO_2$ absorbance, while the second wavelength filter 24b is designed to transmit infrared radiation having a wavelength of about 4412 nm for the measurement of the $^{13}CO_2$ absorbance. The first detection element 25a and the second detection element 25b are adapted for detection of the infrared light beams.

The first wave length filter 24a, the first detection element 25a, the second wave length filter 24b and the second detection element 25b are housed in a package 26 filled with an inert gas such as Ar.

The temperature of the entire infrared detector D is kept at a constant level by a heater and a Peltier element, and the internal temperatures of packages 26a, 26b are each kept at a low level by a Peltier element 27.

Fans 28, 29 are provided for ventilation in the isotopic gas spectrophotometric analyzer.

The reference gas supplying section 30 is annexed to a main body of the isotopic gas spectrophotometric analyzer for supplying air freed of $CO_2$. The reference gas supplying section 30 includes a dust filter 31, a compressor 32, a moisture removing section 33, a dry filter 34, a flow meter 35 and a carbon dioxide absorbing section 36 which are connected in series.

The carbon dioxide absorbing section 36 employs, for example, soda lime (a mixture of sodium hydroxide and calcium hydroxide) as a carbon dioxide absorbent.

Figure 2A:
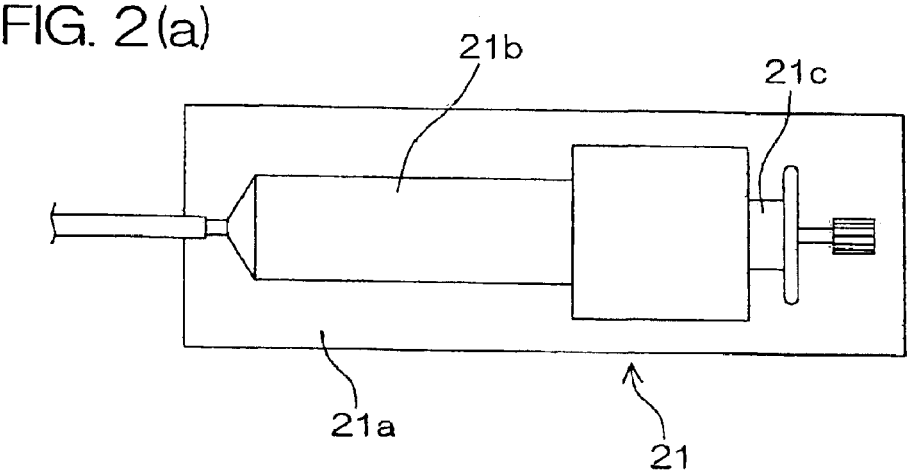
FIG. 2(a) is a plan view illustrating a gas injector 21 for quantitatively injecting a gas specimen.
Figure 2B:
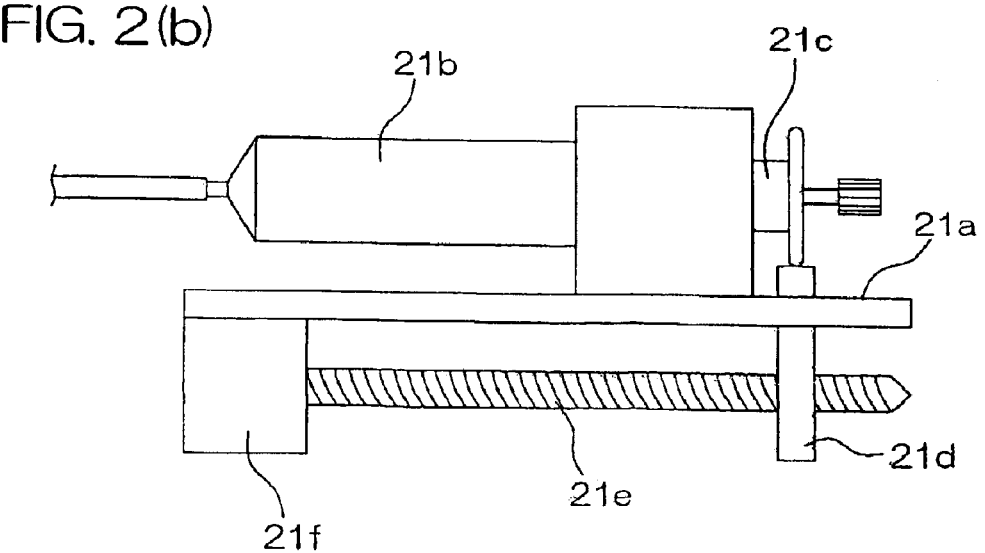
FIG. 2(b) is a front view illustrating the gas injector 21.

FIGS. 2(a) and 2(b) are a plan view and a front view, respectively, illustrating the gas injector 21 for quantitatively injecting a gas specimen. The gas injector 21 functions as "pressurizing means".

The gas injector 21 includes a base 21a, a cylinder 21b provided on the base 21a, a piston 21c fitted in the cylinder 21b, a movable nut 21d provided below the base 21a and coupled to the piston 21c, and a feed screw 21e threadingly engaged with the nut 21d, and a pulse motor 21f for rotating the feed screw 21e.

The pulse motor 21f is driven in a normal direction and a reverse direction by a driver circuit not shown. When the feed screw 21e is rotated by the rotation of the pulse motor 21f, the nut 21d is moved back and forth in accordance with the direction of the rotation of the screw. Thus, the piston 21c is moved back and forth to a desired position. Therefore, the introduction and ejection of the gas specimen into/from the cylinder 21b can be controlled as desired.

III. Measuring Procedure

The measurement is achieved by performing a reference gas measurement process, a base gas measurement process, the reference gas measurement process, a sample gas measurement process, and the reference gas measurement process in this order. In FIGS. 3 to 11, gas flow paths are hatched.

During the measurement, the reference gas constantly flows through the auxiliary cell 11c. The flow rate of the reference gas is kept at a constant level by the flow meter 35.

III-1. Reference Measurement Process

Figure 3:
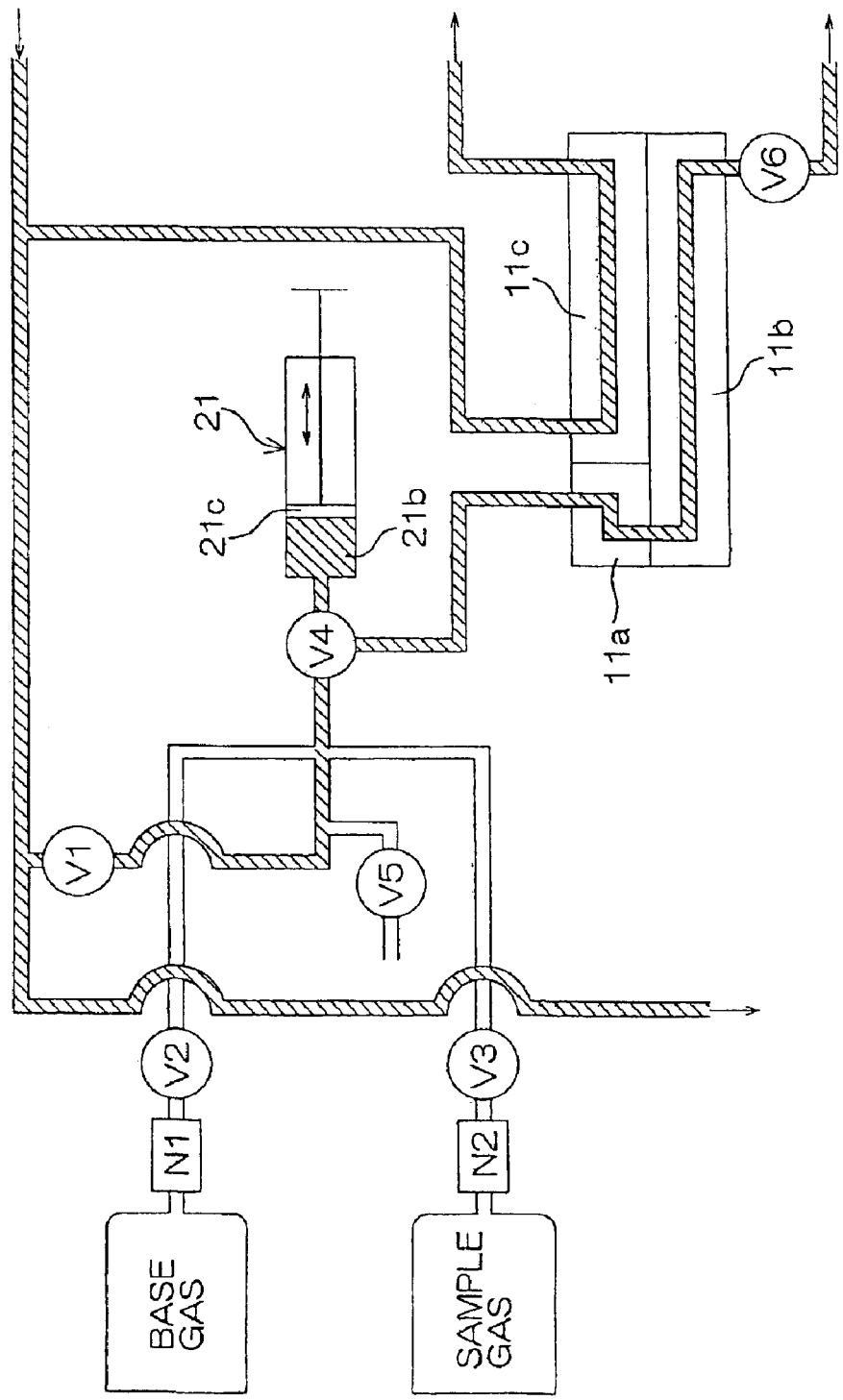
FIG. 3 is a diagram illustrating a gas flow path to be employed when the gas flow path and a cell chamber 11 are cleaned with a clean reference gas.

The clean reference gas is passed through a gas flow path and the cell chamber 11 of the isotopic gas spectrophotometric analyzer as shown in FIG. 3 to clean the gas flow path and the cell chamber 11. At this time, the cylinder 21b is also cleaned by moving back and forth the piston 21c.

Figure 4:
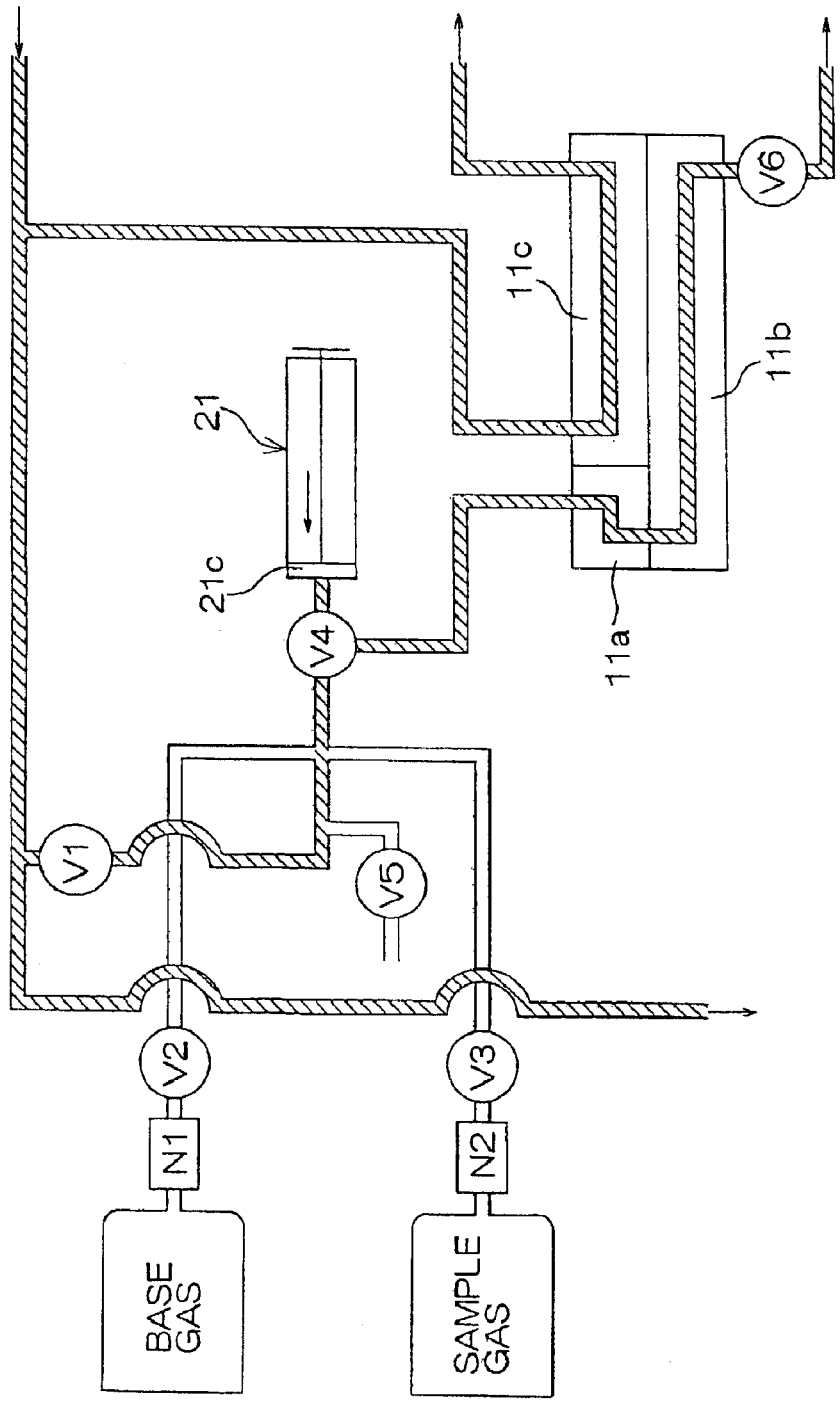
FIG. 4 is diagram illustrating a gas flow path to be employed when a light intensity measuring process is performed on the reference gas.

Then, the reference gas is ejected from the cylinder 21b as shown in FIG. 4, and light intensities are measured by means of the respective detection elements 25a, 25b.

The light intensities thus measured by the first and second detection elements 25a and 25b are represented by $^{12}R1$ and $^{13}R1$, respectively.

III-2. Base Gas Measurement Process

Figure 5:
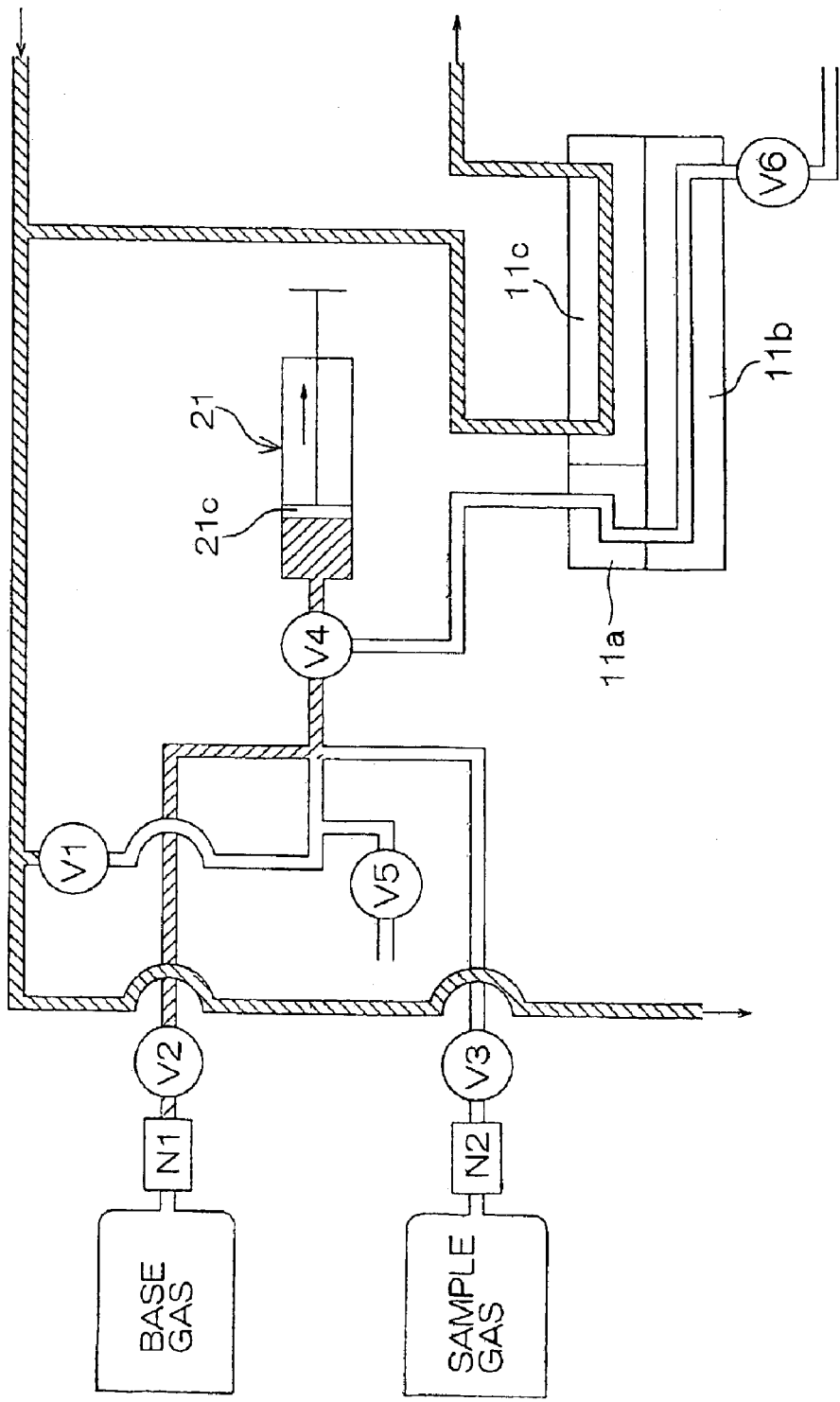
FIG. 5 is a diagram illustrating a gas flow path to be employed when a base gas is sucked into the gas injector 21 from a breath sampling bag.

With the valve V1 being closed and two ports of the valve V4 being open as shown in FIG. 5, the reference gas is prevented from flowing into the first sample cell 11a and the second sample cell 11b. Then, the valve V2 is opened, and the base gas is sucked into the gas injector 21 from the breath sampling bag.

Figure 6:
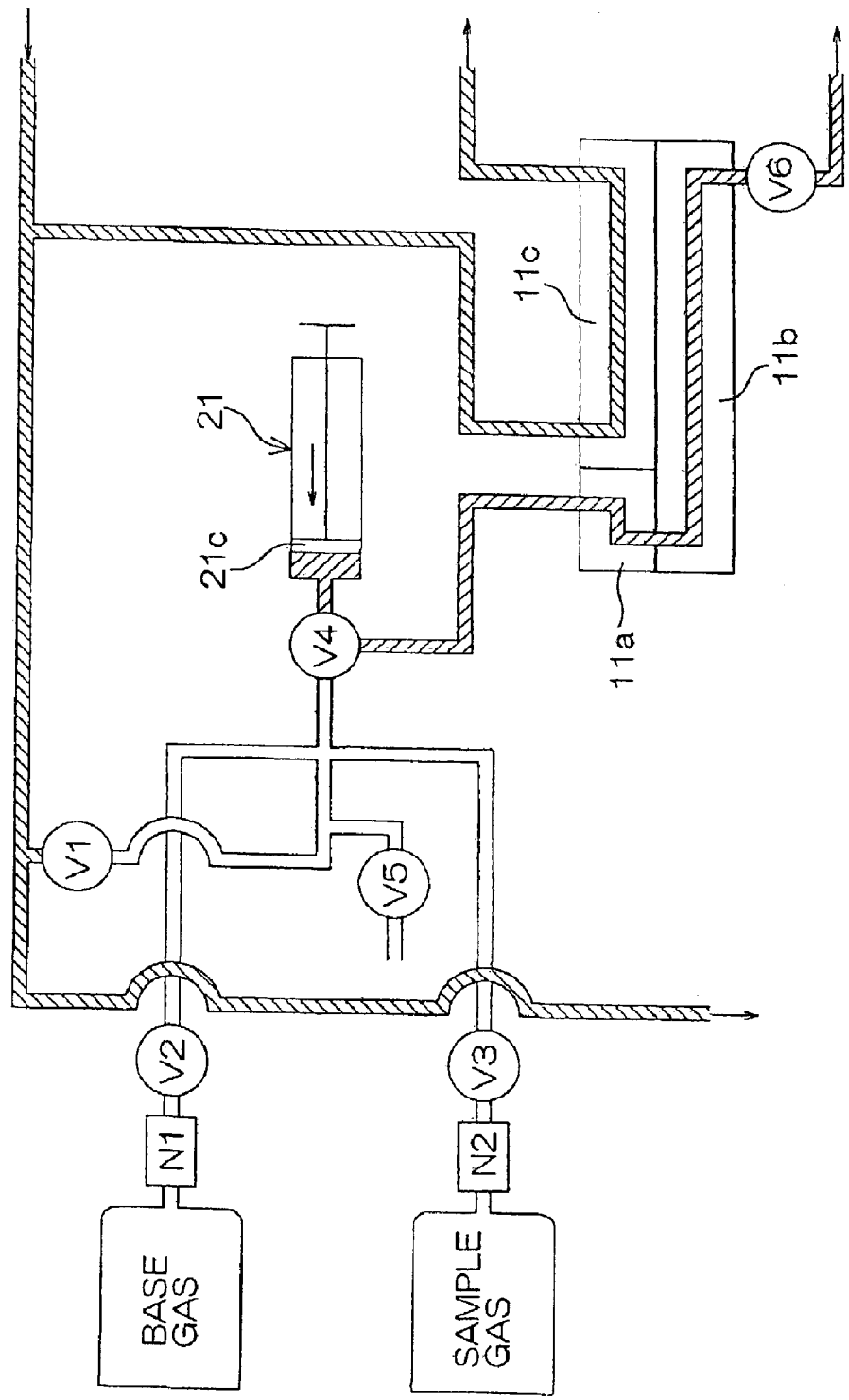
FIG. 6 is a diagram illustrating a gas flow path to be employed when a part of the base gas is mechanically ejected from the gas injector 21 to supply the base gas into a first sample cell 11a and a second sample cell 11b.

After the suction of the base gas, a part of the base gas is mechanically ejected from the gas injector 21 with one port of the valve V4 and the valve V6 being open as shown in FIG. 6, whereby the first sample cell 11a and the second sample cell 11b are filled with the base gas.

Figure 7:
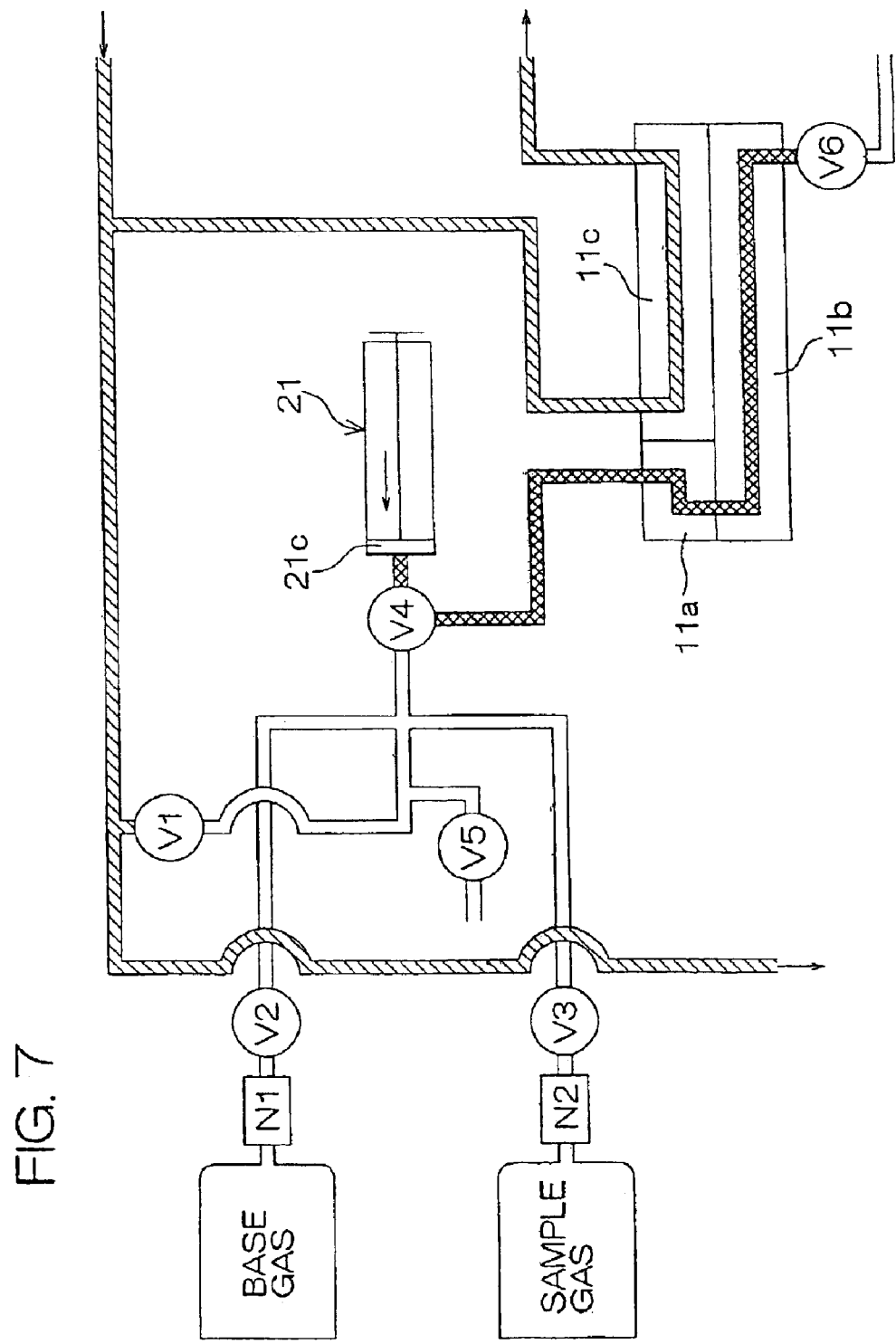
FIG. 7 is a diagram illustrating a gas flow path to be employed when the rest of the base gas is completely ejected from a cylinder 21b with a valve V6 being closed.

Then, the valve V6 is closed as shown in FIG. 7, and the rest of the base gas is completely ejected from the cylinder 21b. Thus, the base gas pressure in the first sample cell 11a and the second sample cell 11b is increased. In FIG. 7, a gas flow path containing the higher pressure gas is cross-hatched.

In this pressurized state, light intensities are measured by the respective detection elements 25a, 25b.

The light intensities thus measured by the first and second detection elements 25a and 25b are represented by $^{12}B$ and $^{13}B$, respectively.

III-3. Reference Measurement Process

The cleaning of the gas flow path and the cells and the light intensity measurement for the reference gas are performed again (see FIGS. 3 and 4).

Light intensities thus measured by the first and second detection elements 25a and 25b are represented by $^{12}R2$ and $^{13}R2$, respectively.

III-4. Sample Gas Measurement Process

Figure 8:
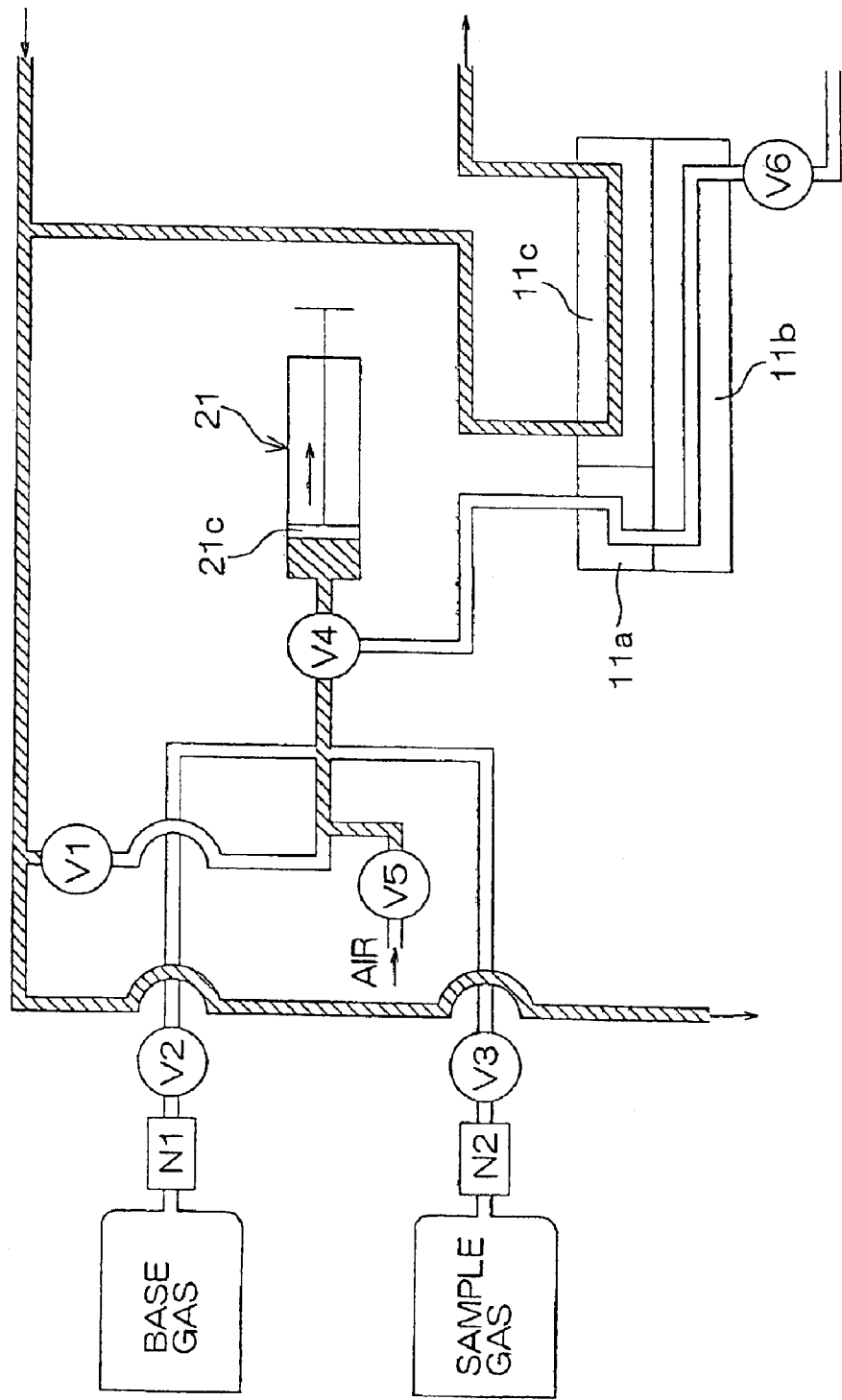

Air for sample gas dilution is sucked into the gas injector 21 with the valve V5 being open as shown in FIG. 8. When the $CO_2$ concentration in the sample gas is higher than the $CO_2$ concentration in the base gas, the sample gas is diluted so that these $CO_2$ concentrations are equalized with each other.

If the $CO_2$ concentration in the base gas is higher than the $CO_2$ concentration in the sample gas, the base gas is diluted prior to the suction of the base gas (see FIG. 5)

The $CO_2$ concentration in the base gas and the $CO_2$ concentration in the sample gas are preliminarily determined through the light intensity measurement by means of the detection elements 25a, 25b.

For detailed information on the dilution process, see International Publication WO98/30888.

Figure 9:
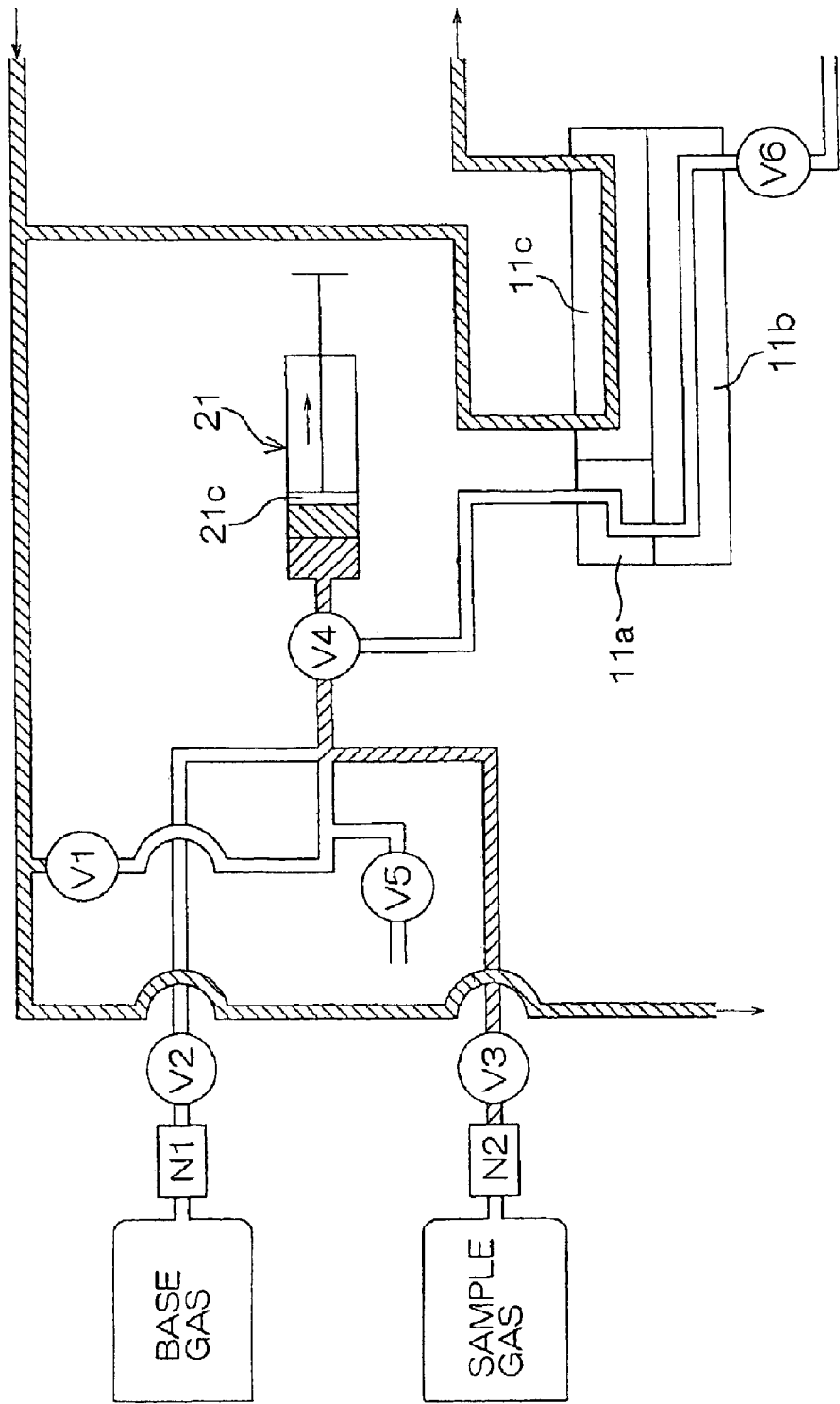
FIG. 9 is a diagram illustrating a gas flow path to be employed when a sample gas is sucked in to the gas injector 21 from another breath sampling bag.

Then, the sample gas is sucked into the gas injector 21 from the breath sampling bag with the reference gas being prevented from flowing into the first sample cell 11a and the second sample cell 11b (see FIG. 9). Thus, the sample gas is diluted in the cylinder 21b.

Figure 10:
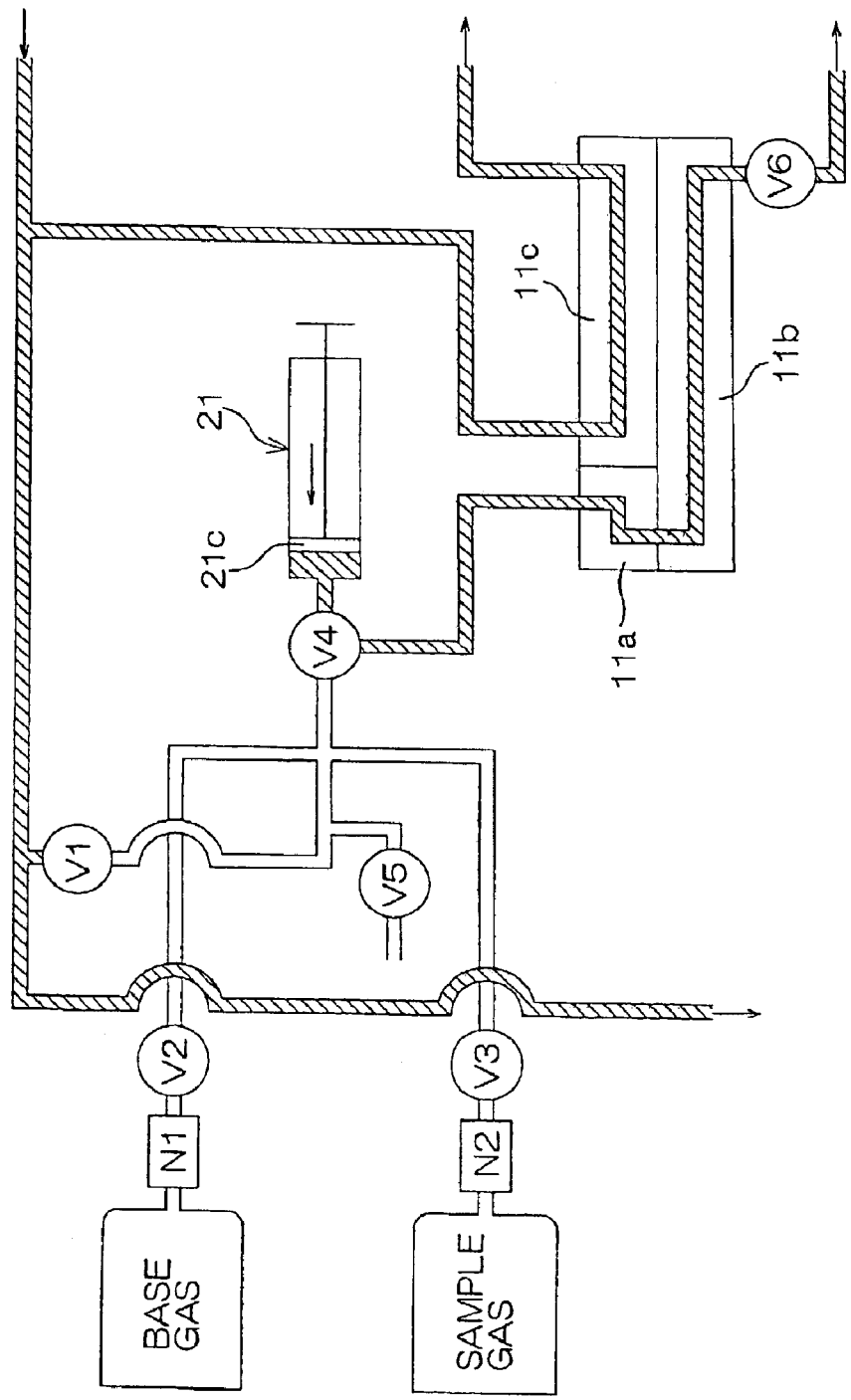
FIG. 10 is a diagram illustrating a gas flow path to be employed when the sample gas is supplied into the first sample cell 11a and the second sample cell 11b.

After the suction of the sample gas, the first sample cell 11a and the second sample cell 11b are filled with the sample gas as shown in FIG. 10.

Figure 11:
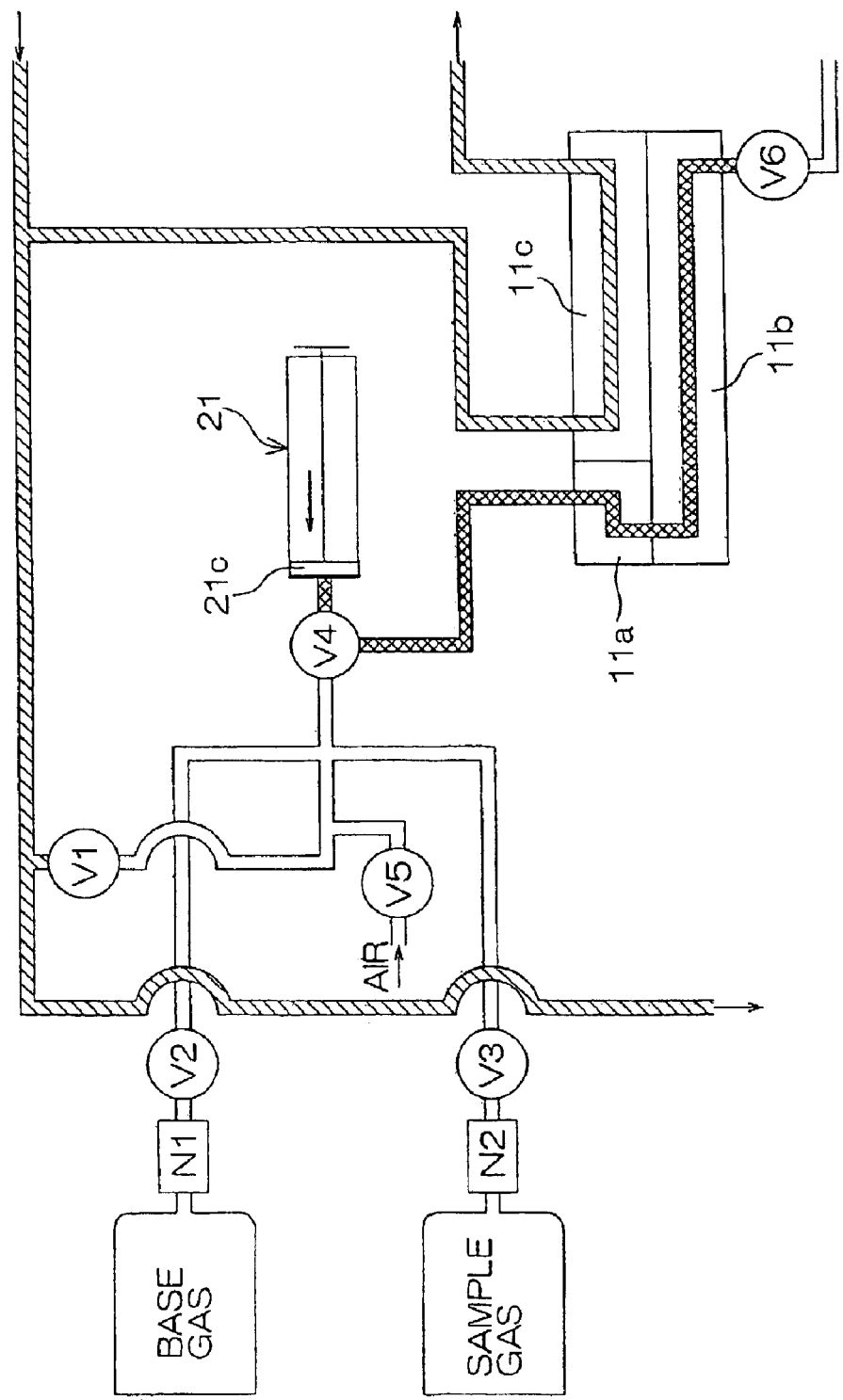
FIG. 11 is a diagram illustrating a gas flow path to be employed when the sample gas is pressurized in the first sample cell 11a and the second sample cell 11b with the valve V6 being closed.

Then, the valve V6 is closed as shown in FIG. 11, and the sample gas is mechanically ejected from the gas injector 21, whereby the sample gas is pressurized in the first sample cell 11a and the second sample cell 11b.

The operation of the gas injector 21 is stopped, and then light intensities are measured by the detection elements 25a, 25b.

The light intensities thus measured by the first and second detection elements 25a and 25b are represented by $^{12}S$ and $^{13}S$, respectively.

III-5. Reference Measurement Process

The cleaning of the gas flow path and the cells and the light intensity measurement for the reference gas are performed again (see FIGS. 3 and 4).

Light intensities thus measured by the first and second detection elements 25a and 25b are represented by $^{12}R3$ and $^{13}R3$, respectively.

IV. Data Processing

IV-1. Calculation of Base Gas Absorbances

The $^{12}CO_2$ absorbance $^{12}Abs(B)$ and the $^{13}CO_2$ absorbance $^{13}Abs(B)$ of the base gas are calculated on the basis of the transmitted light intensities $^{12}R1$ and $^{13}R1$ for the reference gas, the transmitted light intensities $^{12}B$ and $^{13}B$ for the base gas and the transmitted light intensities $^{12}R2$ and $^{13}R2$ for the reference gas.

The $^{12}CO_2$ absorbance $^{12}Abs(B)$ is calculated from the following equation:

$$^{12}\text{Abs}(B) = -\log[2 \cdot {}^{12}B/({}^{12}R1 + {}^{12}R2)]$$

The $^{13}CO_2$ absorbance $^{13}Abs(B)$ is calculated from the following equation:

$$^{13}\text{Abs}(B) = -\log[2 \cdot {}^{13}B/({}^{13}R1 + {}^{13}R2)]$$

Since the calculation of the absorbances is based on the light intensities obtained in the base gas measurement process and the averages (R1+R2)/2 of the light intensities obtained in the reference measurement processes performed before and after the base gas measurement process, the influence of a drift (a time-related influence on the measurement) can be eliminated. Therefore, there is no need for waiting until the analyzer reaches a complete thermal equilibrium. (which usually takes several hours) at the start-up of the analyzer. Thus, the measurement can be started immediately after the start-up of the analyzer.

IV-2. Calculation of Sample Gas Absorbances

The $^{12}CO_2$ absorbance $^{12}Abs(S)$ and the $^{13}CO_2$ absorbance $^{13}Abs(S)$ of the sample gas are calculated on the basis of the transmitted light intensities $^{12}R2$ and $^{13}R2$ for the reference gas, the transmitted light intensities $^{12}S$ and $^{13}S$ for the sample gas and the transmitted light intensities $^{12}R3$ and $^{13}R3$ for the reference gas.

The $^{12}CO_2$ absorbance $^{12}Abs(S)$ is calculated from the following equation:

$$^{12}\text{ABS}(S) = -\log[2 \cdot {}^{12}S/({}^{12}R2 + {}^{12}R3)]$$

The $^{13}CO_2$ absorbance $^{13}Abs(S)$ is calculated from the following equation:

$$^{13}\text{ABS}(S) = -\log[2 \cdot {}^{13}S/({}^{13}R2 + {}^{13}R3)]$$

Since the calculation of the absorbances is based on the light intensities obtained in the sample gas measurement process and the averages of the light intensities obtained in the reference measurement processes performed before and after the sample gas measurement process, the influence of a drift can be eliminated.

IV-3. Calculation of Concentrations

The $^{12}CO_2$ concentration and the $^{13}CO_2$ concentration are determined with the use of a calibration curve. The calibration curve is prepared on the basis of measurement performed by using gas samples of known $^{12}CO_2$ concentrations and gas samples of known $^{13}CO_2$ concentrations. Since the base gas and the sample gas are pressurized during the aforesaid measurement processes, these gas samples for the preparation of the calibration curve are also pressurized during the measurement.

For the preparation of the calibration curve, the $^{12}CO_2$ absorbances for different $^{12}CO_2$ concentrations ranging from about 0% to about 6% are measured. The $^{12}CO_2$ concentration and the $^{12}CO_2$ absorbance are plotted as abscissa and ordinate, respectively, and the curve is determined by the method of least squares. An approximate quadratic curve, which includes relatively small errors, is employed as the calibration curve in this embodiment.

The $^{12}CO_2$ concentration and $^{13}CO_2$ concentration in the base gas and the $^{12}CO_2$ concentration and $^{13}CO_2$ concentration in the sample gas determined by using the aforesaid calibration curve are represented by $^{12}Conc(B)$, $^{13}Conc(B)$, $^{12}Conc(S)$ and $^{13}Conc(S)$, respectively.

IV-4. Calculation of Concentration Ratios

The concentration ratio of $^{13}CO_2$ to $^{12}CO_2$ is determined. The concentration ratios in the base gas and in the sample gas are expressed as $^{13}Conc(B)/{}^{12}Conc(B)$ and $^{13}Conc(S)/{}^{12}Conc(S)$, respectively.

Alternatively, the concentration ratios may be defined as $^{13}Conc(B)/({}^{12}Conc(B)+{}^{13}Conc(B))$ and $^{13}Conc(S)/({}^{12}Conc(S)+{}^{13}Conc(S))$. Since the $^{12}CO_2$ concentration is much higher than the $^{13}CO_2$ concentration, the concentration ratios expressed in the former way and in the latter way are virtually the same.

IV-5. Determination of $^{13}C$ change

A $^{13}C$ difference between the sample gas and the base gas is calculated from the following equation:

$\Delta^{13}C=$[(Concentration ratio in sample gas)−(Concentration ratio in base gas)]×$10^3$/(Concentration ratio in base gas) (Unit: per mil(per thousand))

V. Judgment of Absorption Capacity of Carbon Dioxide Absorbent

An explanation will next be given to a procedure for judging the absorption capacity of the carbon dioxide absorbent. In FIGS. 12 to 15, gas flow paths are hatched.

During measurement, the reference gas is constantly passed through the auxiliary cell 11c, and the flow rate of the reference gas is kept at a constant level by the flow meter 35.

V-1. Air Light Intensity Measurement Process

Figure 12:
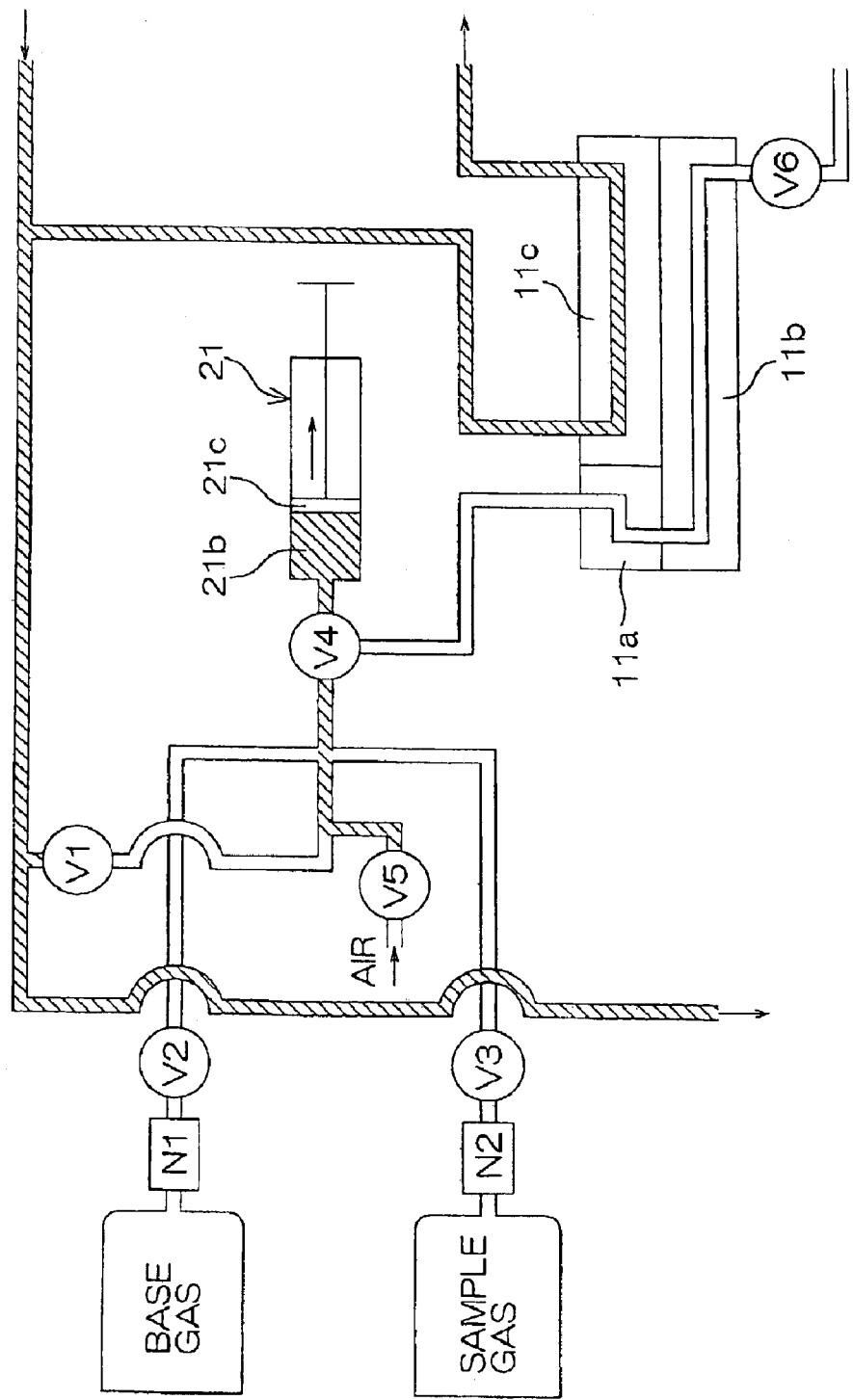
FIG. 12 is a diagram illustrating a gas flow path to be employed when air is sucked into the cylinder 21b.

Air is sucked into the cylinder 21b with the valve V1 being closed and the Valve V5 and two ports of the valve V4 being open as shown in FIG. 12.

Figure 13:
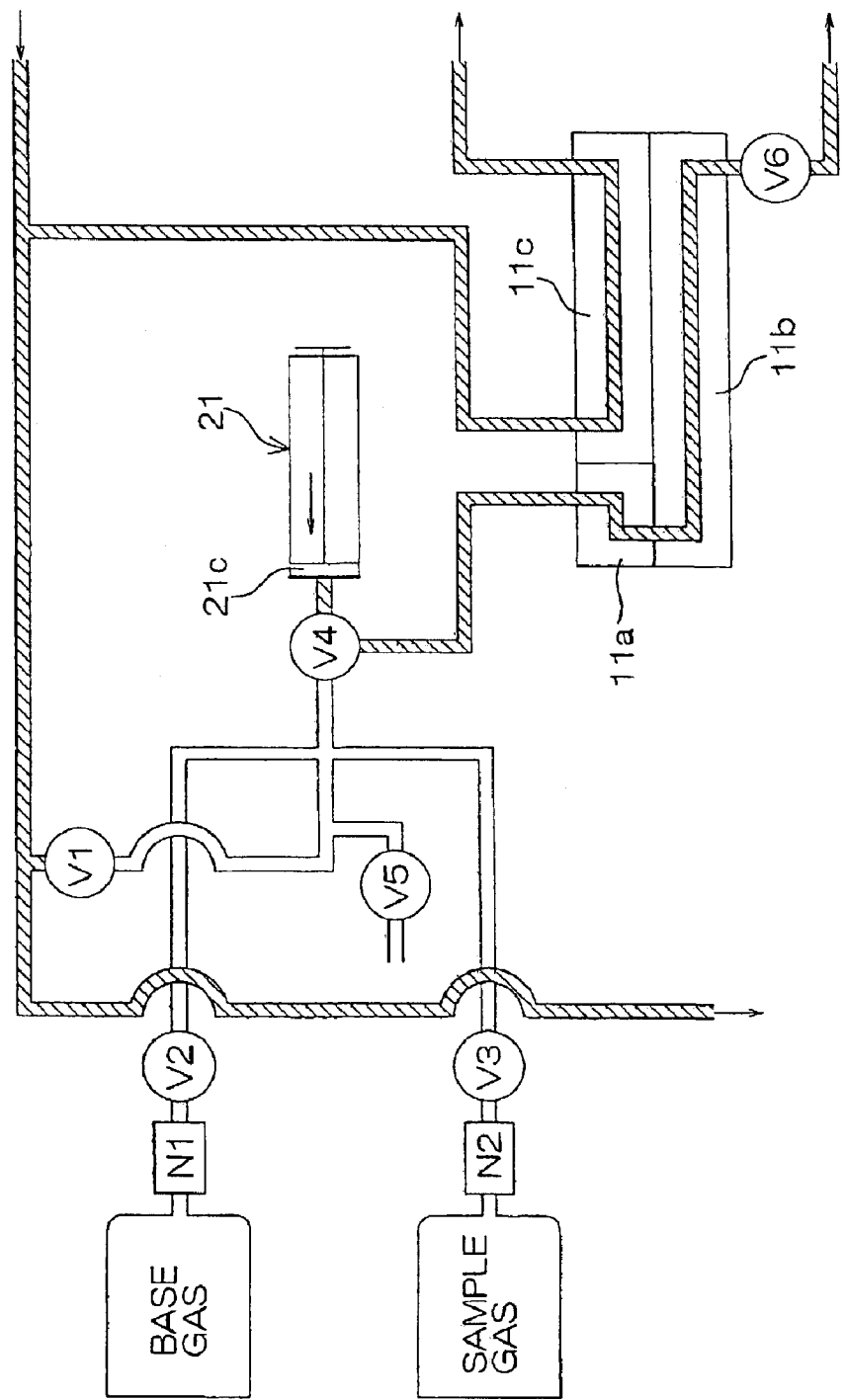
FIG. 13 is a diagram illustrating a gas flow path to be employed when the air is ejected at a constant flow rate from the cylinder 21b for the light intensity measuring process.

The valve V4 is switched as shown in FIG. 13, and air is ejected at a constant flow rate from the cylinder 21b into the gas flow path and the cell chamber 11 of the isotopic gas spectrophotometric analyzer. Then, a light intensity is measured by the detection element 25a.

The light intensity thus measured by the first detection element 25a is represented by $^{12}A$.

V-2. Reference Gas Measurement Process

Figure 14:
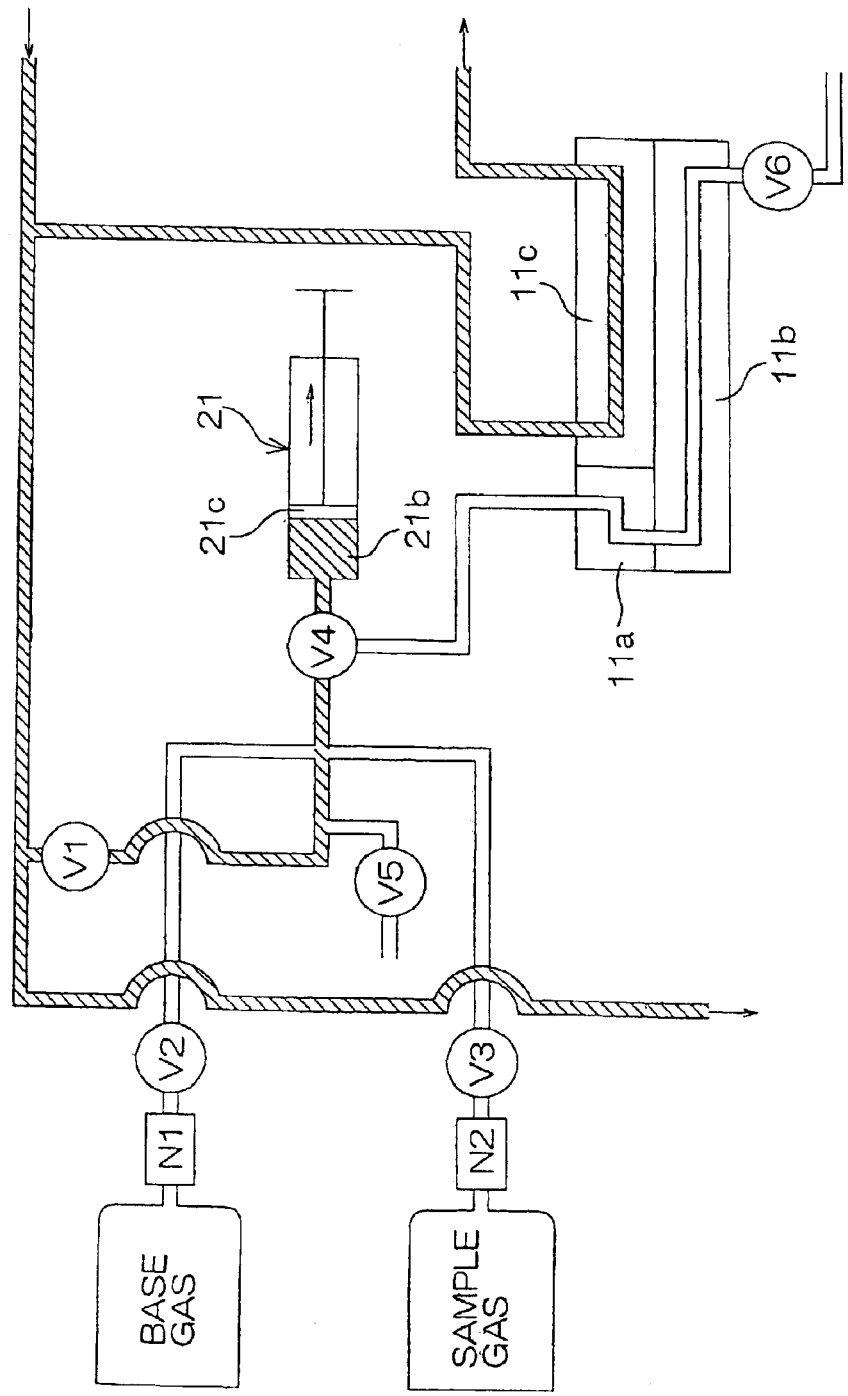
FIG. 14 is a diagram illustrating a gas flow path to be employed when the reference gas is sucked into the gas injector 21.

The reference gas is sucked into the gas injector 21 with the valve V1 and two ports of the valve V4 being open as shown in FIG. 14.

Figure 15:
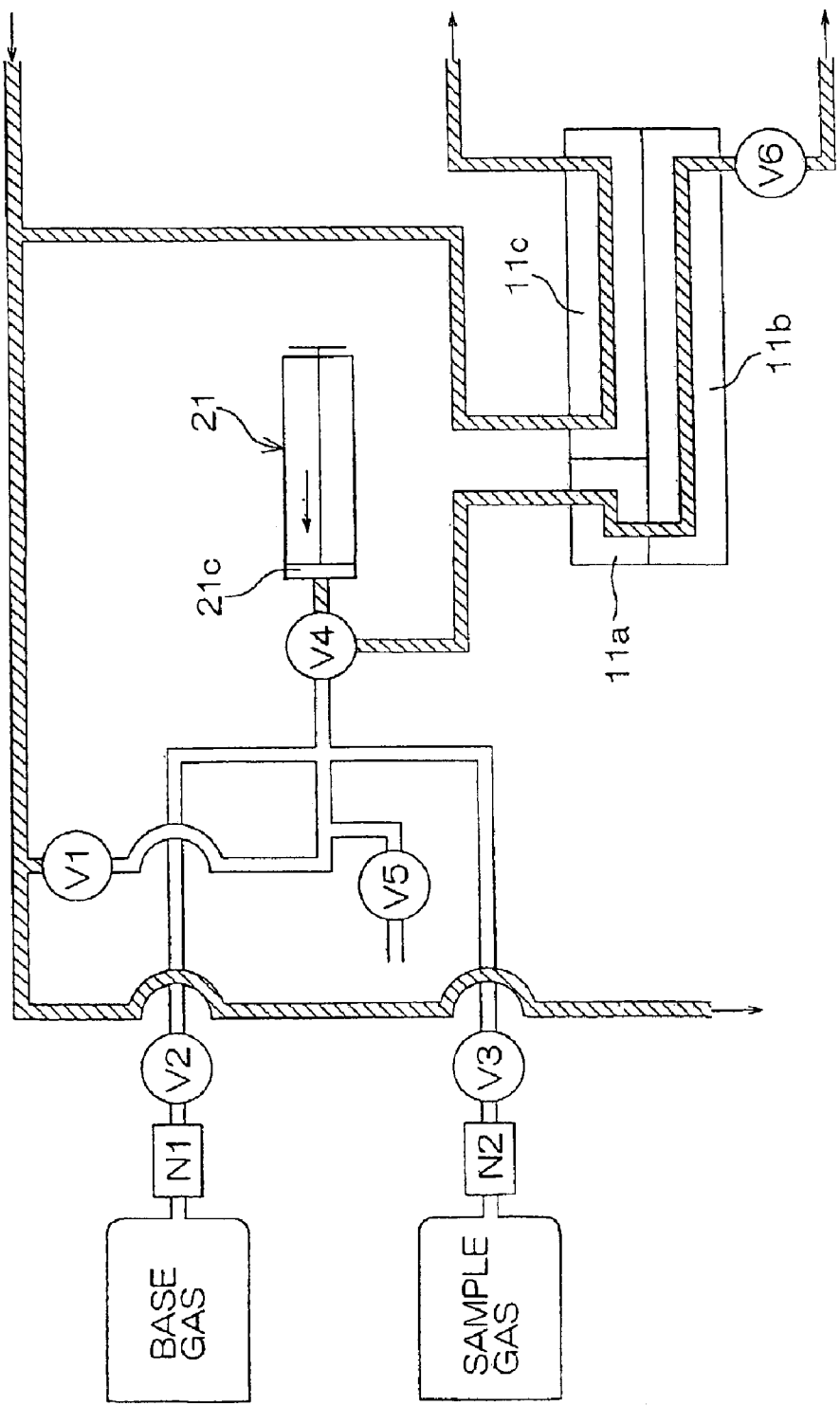
FIG. 15 is a diagram illustrating a gas flow path to be employed when the reference gas is filled in the first sample cell 11a and the second sample cell 11b with the use of the gas injector 21.

After the suction of the base gas, the valve V4 is switched as shown in FIG. 15, and the base gas is mechanically ejected at a constant flow rate from the gas injector 21. Thus, the first sample cell 11a and the second sample cell 11b are filled with the reference gas. In this state, a light intensity is measured by the detection element 25a.

The light intensity thus measured by the first detection element 25a is represented by $^{12}R$.

V-3. Data Processing

A $^{12}CO_2$ intensity ratio $^{12}$Ratio is determined on the basis of the transmitted light intensity $^{12}A$ for air and the transmitted light intensity $^{12}R$ for the reference gas. The intensity ratio $^{12}$Ratio is calculated from the following equation:

$$^{12}\text{Ratio}=^{12}A/^{12}R$$

As the intensity ratio $^{12}$Ratio approches 1, the absorption capacity of the carbon dioxide absorbent is reduced. More specifically, there is a relationship between the intensity ratio and the absorption capacity as shown in Table 1.

TABLE 1

| $^{12}$Ratio | Absorption capacity |
|---|---|
| 0.980 | 100% |
| 0.990 | 50% |
| 1.000 | 0% |

The absorption capacity of the carbon dioxide absorbent can be judged on the basis of the thus determined intensity ratio $^{12}$Ratio with reference to Table 1.

When the intensity ratio $^{12}$Ratio is lower than a threshold (e.g. 0.990), an indication of the deterioration of the carbon dioxide absorbent is displayed on a liquid crystal display device (not shown) of the isotopic gas analyzer for information to a user. Further, the isotopic gas spectrophotometric analysis is not permitted until the carbon dioxide absorbent is replaced.

EXAMPLE 1

Changes $\Delta^{13}C$ were determined for a gas specimen having a $^{12}CO_2$ concentration of 1% with the gas specimen being pressurized at a plurality of levels and without the pressurization of the gas specimen.

The gas specimen employed in this example was not a breath sample of a patient as the sample gas or the base gas, but was air of 1% $^{12}CO_2$ concentration contained in a single breath sampling bag having a greater size. The breath sampling bag had two outlets, which were respectively connected to the nozzles N1 and N2. Since the same gas specimen was employed for the measurement in this example, the changes $\Delta^{13}C$ should have normally been zero.

Table 2 shows the changes $\Delta^{13}C$ calculated on the basis of measurement results obtained when the measurement was performed ten times by additionally injecting the gas in amounts of 0 ml (1 atm), 5 ml (about 1.25 atom), 10 ml (about 1.5 atm), 15 ml (about 1.75 atm) and 20 ml (about 2 atm).

TABLE 2

| | | | | | (%) |
|---|---|---|---|---|---|
| Number of times of | Additionally injected amount (ml) | | | | |
| measurement | 0 | 5 | 10 | 15 | 20 |
| 1 | 0.6 | 1.3 | 0.9 | 0.1 | −0.5 |
| 2 | 1.2 | 0.3 | −0.4 | 0.1 | 0.1 |
| 3 | −0.5 | 0.9 | 0.1 | 0.4 | 0.0 |
| 4 | 0.0 | −0.5 | −0.2 | −0.1 | 0.1 |
| 5 | 0.6 | 0.9 | −0.2 | −0.5 | −0.6 |
| 6 | −0.8 | −0.1 | −0.1 | −0.3 | 0.0 |
| 7 | −0.6 | 0.1 | 0.9 | −0.7 | 0.0 |
| 8 | −0.4 | 0.4 | −0.3 | 0.0 | −0.1 |
| 9 | 0.6 | 0.0 | 0.6 | 0.1 | −0.4 |
| 10 | 0.9 | 0.8 | −0.1 | −0.3 | −0.3 |
| Average | 0.16 | 0.41 | 0.12 | −0.12 | −0.17 |
| Standard deviation | 0.71 | 0.56 | 0.49 | 0.33 | 0.26 |
| Maximum value | 1.2 | 1.3 | 0.9 | 0.4 | 0.1 |
| Minimum value | −0.8 | −0.5 | −0.4 | −0.7 | −0.6 |

Figure 16:
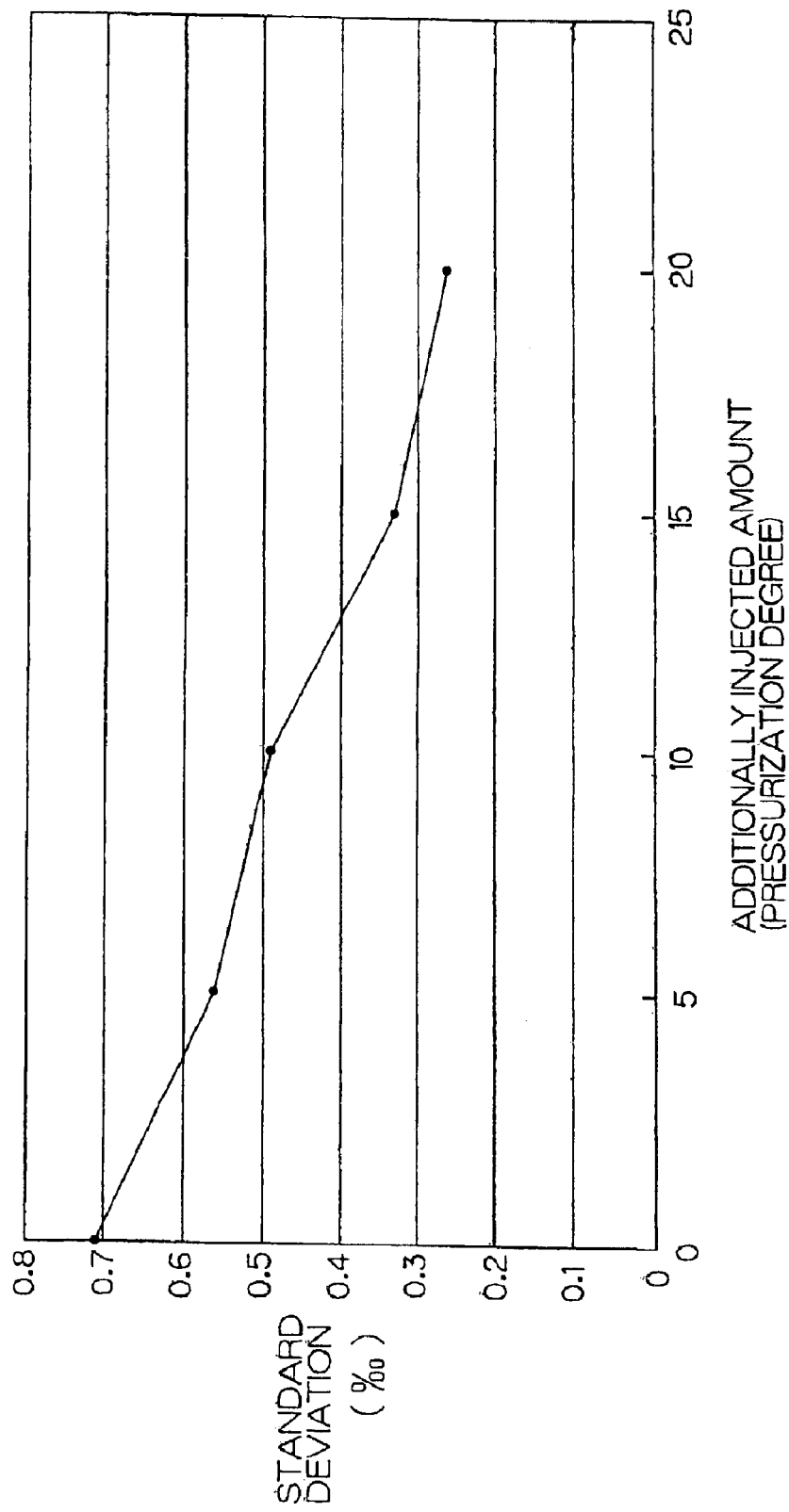
FIG. 16 is a graph illustrating a relationship between an additionally injected amount (pressurization degree) of the gas specimen and a standard deviation indicative of variations in $\Delta^{13}C$ data.

A relationship between the additionally injected amount and a standard deviation indicative of variations in the $\Delta^{13}C$ data is shown in FIG. 16.

As can be seen in FIG. 16, there was an obvious correlation between the additionally injected amount and the standard deviation. As the additionally injected amount (pressurization degree) increased, the standard deviation was reduced.

Therefore, the pressurization effectively improves the reproducibility of the measurement data.

EXAMPLE 2

Soda lime (a mixture of sodium hydroxide and calcium hydroxide) was used as the carbon dioxide absorbent. Reactions are shown below.

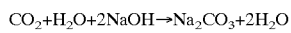

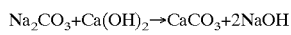

Figure 17:
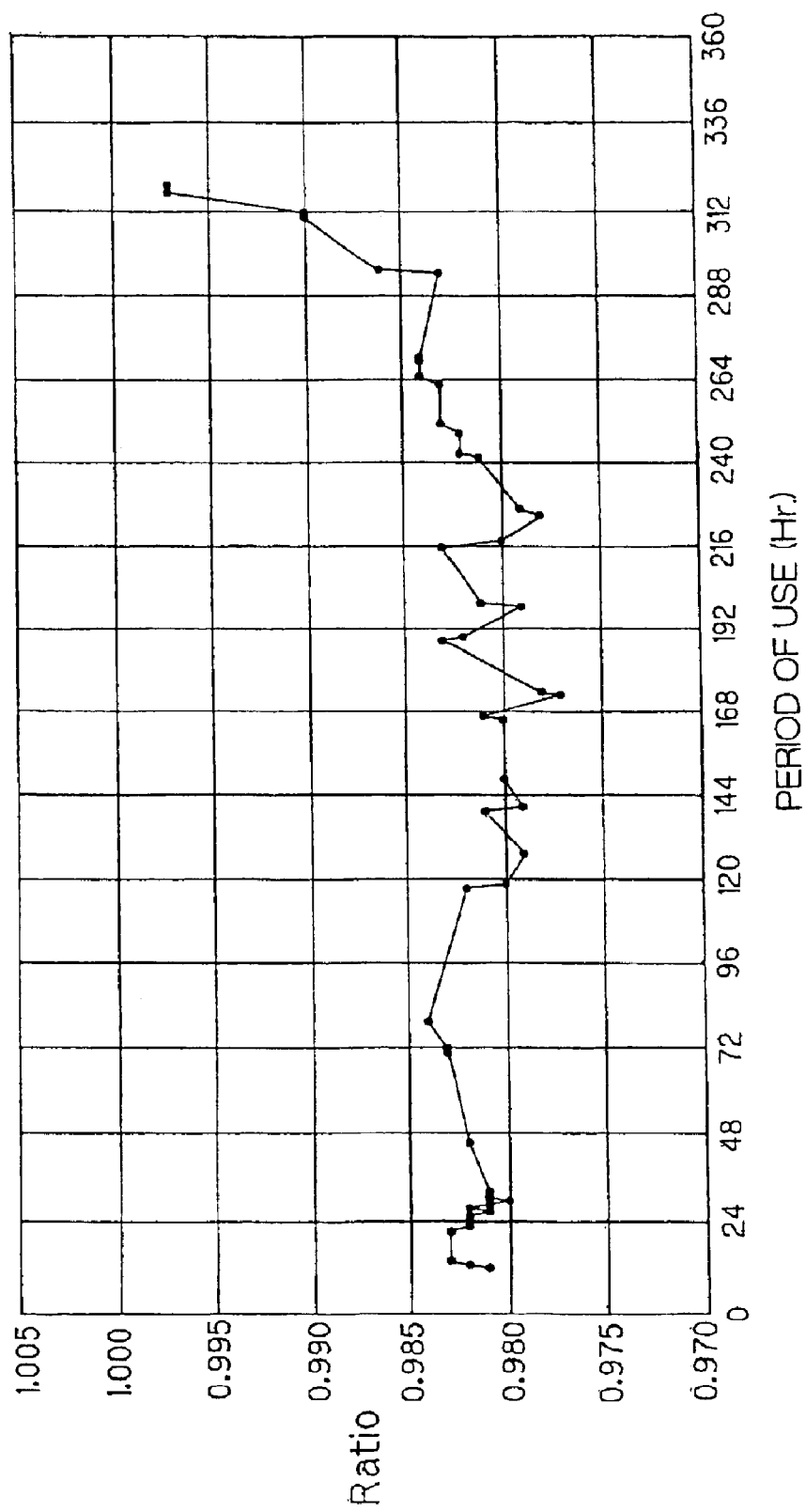
FIG. 17 is a graph obtained by plotting a relationship between the total period of use of a carbon dioxide absorbent and an intensity ratio $^{12}$Ratio.

The measurement was performed a plurality of times a day, and a relationship between the total period of the use of the carbon dioxide absorbent and the intensity ratio $^{12}$Ratio was plotted in a graph as shown in FIG. 17. As can be seen in FIG. 17, the intensity ratio $^{12}$Ratio steeply increased when the total period exceeded about 300 hours.

In addition to the aforesaid measurement, measurement was performed by employing a reference gas prepared with the use of the same carbon dioxide absorbent and a gas specimen having a $^{12}CO_2$ concentration of 1% as the sample gas, and changes $\Delta^{13}C$ in $^{13}C$ were calculated. The gas specimen employed in this example was not a breath sample of a patient as the sample gas or the base gas, but was air of 1% $^{12}CO_2$ concentration contained in a single breath sampling bag having a greater size. The breath sampling bag had two outlets, which were respectively connected to the nozzles N1 and N2.

More specifically, the $^{12}CO_2$ absorbance $^{12}Abs$ and the $^{13}CO_2$ absorbance $^{13}Abs$ were respectively calculated from the following equations:

$$^{12}ABS = -\log[^{12}S/^{12}R]$$

$$^{13}ABS = -\log[^{13}S/^{13}R]$$

wherein $^{12}S$ and $^{13}S$ are transmitted light intensities for the gas specimen, and $^{12}R$ and $^{13}R$ are transmitted light intensities for the reference gas. With the use of the calibration curve, a $^{12}CO_2$ concentration $^{12}Conc$ and a $^{13}CO_2$ concentration $^{13}Conc$ were determined, and then a concentration ratio $^{13}Conc/^{12}Conc$ was calculated.

This procedure was performed again for the same gas specimen. A change $\Delta^{13}C$ was calculated from the following equation:

$$\Delta^{13}C = [(\text{Concentration ratio at first time}) - (\text{Concentration ratio at second time})] \times 10^3/(\text{Concentration ratio at first time}) \text{ (Unit: per mil(per thousand))}$$

The aforesaid procedure was repeated 10 times for calculation of the changes $\Delta^{13}C$.

Since the same gas specimen was employed in this example, the changes $\Delta^{13}C$ should have normally been zero. However, there were deviations of measurement data from zero due to measurement errors. Standard deviations SD were plotted in a graph as shown in FIG. 18.

Figure 18:
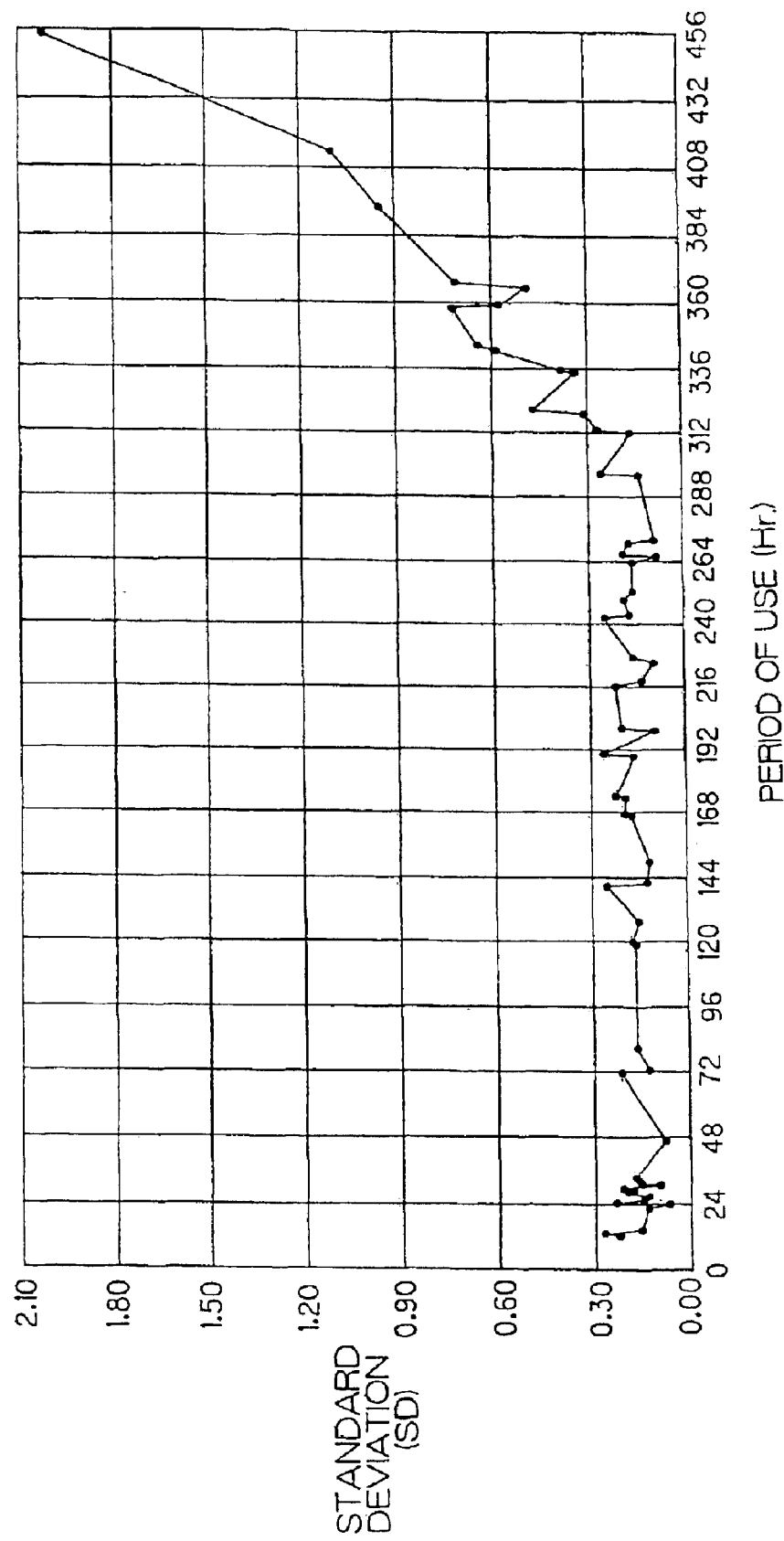
FIG. 18 is a graph obtained by plotting a relationship between the total period of the use of the carbon dioxide absorbent and a standard deviation SD of $\Delta^{13}C$ data indicative of changes $\Delta^{13}C$ in $^{13}C$ calculated on the basis of a plurality of measurements.

As can be seen in FIG. 18, the standard deviation SD indicative of variations in the measurement data exceeded 0.30 and steeply increased after the total use period reached 300 hours.

In the graph shown in FIG. 17, a total use period of 300 hours corresponds to an intensity ratio $^{12}Ratio$ of 0.99, which is a reference value to be employed as the threshold for the replacement of the carbon dioxide absorbent. The value "0.99" is merely an example, so that a different threshold may of course be employed depending on the specifications of the analyzer.

What is claimed is:

1. A stable isotope measurement method for spectrometrically analyzing an isotopic gas by introducing a gas specimen containing a plurality of component gases into a cell, measuring intensities of light transmitted therethrough at wavelengths suitable for the respective component gases, and processing data of the light intensities to determine a concentration ratio between the component gases, the component gases being carbon dioxide $^{12}CO_2$ and carbon dioxide $^{13}CO_2$, the method comprising:

a first step of introducing the gas specimen into the cell and into a gas injector which is communicated with the cell;

a second step of injecting the gas specimen by the gas injector in a predetermined amount in the cell and pressurizing the gas specimen in the cell;

a third step of determining absorbances of light transmitted therethrough at the wavelengths suitable for the respective component gases; and a fourth step of determining a concentration ratio between the component gases in the gas specimen on the basis of a calibration curve prepared through measurement on pressurized gas samples each containing the component gases in known concentrations.

2. (amended) A stable isotope measurement method for spectrometrically analyzing an isotopic gas as set forth in claim 1, wherein the gas specimen is pressurized up to 2 atm in the cell.

3. A method of judging the absorption capacity of a carbon dioxide absorbent for use in an isotopic gas analyzing method for measuring the concentration of carbon dioxide $^{13}CO_2$ in a gas specimen containing carbon dioxide $^{13}CO_2$ and carbon dioxide $^{12}CO_2$ as component gases, the isotopic gas analyzing method comprising the steps of: introducing the gas specimen into cells and measuring the intensities of light beams transmitted through the cells at wavelengths suitable for analysis of the respective component gases; introducing air having passed through a vessel containing the carbon dioxide absorbent as a reference gas into the cells and measuring the intensities of light beams transmitted through the cells at the wavelengths suitable for the analysis of the respective component gases; and processing data indicative of the measurement results, characterized by steps of:

performing a first light intensity measuring process by introducing air having passed through the vessel containing the carbon dioxide absorbent into the cells;

performing a second light intensity measuring process by introducing air not having passed through the vessel containing the carbon dioxide absorbent into the cells; and judging the absorption capacity of the carbon dioxide absorbent on the basis of a light intensity measured in the first light intensity measuring step and a light intensity measured in the second light intensity measuring step.

4. An absorption capacity judging method as set forth in claim 3, wherein the absorption capacity judging step comprises the step of comparing the ratio of the light intensity measured in the first light intensity measuring step to the light intensity measured in the second light intensity measuring step with a threshold.

5. An absorption capacity judging method as set forth in claim 3, wherein the light intensities are measured at a wavelength suitable for analysis of carbon dioxide $^{12}CO_2$ in the first and second light intensity measuring steps.

* * * * *

UNITED STATES PATENT AND TRADEMARK OFFICE
CERTIFICATE OF CORRECTION

PATENT NO. : 6,940,083 B2
DATED : September 6, 2005
INVENTOR(S) : Masaaki Mori et al.

It is certified that error appears in the above-identified patent and that said Letters Patent is hereby corrected as shown below:

<u>Title page,</u>
Item [54], Title, should read -- A STABLE ISOTOPE MEASUREMENT METHOD FOR SPECTROMETRICALLY ANALYZING AN ISOTOPIC GAS AND METHOD OF JUDGING ABSORPTION CAPACITY OF CARBON DIOXIDE ABSORBENT. --.

Signed and Sealed this

Fourteenth Day of March, 2006

JON W. DUDAS
*Director of the United States Patent and Trademark Office*